United States Patent [19] [11] 3,959,259
Breuer [45] May 25, 1976

[54] 1,2,4-OXADIAZOLONYLACETYL PENICILLINS

[75] Inventor: Hermann Breuer, Regensburg, Germany

[73] Assignee: E. R. Squibb & Sons, Inc., Princeton, N.J.

[22] Filed: Oct. 9, 1975

[21] Appl. No.: 621,174

Related U.S. Application Data

[60] Division of Ser. No. 486,542, July 8, 1974, Pat. No. 3,929,782, which is a continuation-in-part of Ser. No. 450,929, March 13, 1974, abandoned.

[52] U.S. Cl. .............................................. 260/239.1
[51] Int. Cl.² .......................................... C07D 499/76
[58] Field of Search ................................. 260/239.1

[56] References Cited
UNITED STATES PATENTS 3,516,997  6/1970  Takano et al. .................. 260/243 C
3,622,568  11/1971  Bamberg et al. ................. 260/239.1

Primary Examiner—Gerald A. Schwartz
Attorney, Agent, or Firm—Lawrence S. Levinson; Merle J. Smith; Stephen B. Davis

[57] ABSTRACT 1,2,4-Oxadiazolonylacetyl penicillins and cephalosporins of the general formula

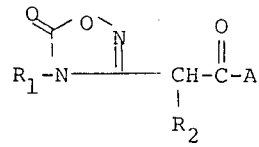

wherein A is either

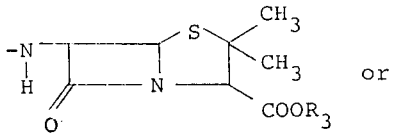

or

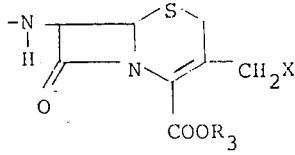

$R_1$ is hydrogen, lower alkyl or phenyl-lower alkyl; $R_2$ is hydrogen, lower alkyl, phenyl, hydroxyphenyl, thienyl, furyl, or pyridyl; $R_3$ is hydrogen, lower alkyl, phenyl-lower alkyl, a salt forming ion, trimethylsilyl, benzhydryl, or

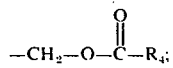

$R_4$ is lower alkyl, phenyl or phenyl-lower alkyl; and X is hydrogen, lower alkoxy, lower alkanoyloxy, lower alkylmercapto, the radical of a nitrogen base, or certain heterocyclic thio moieties; are disclosed. They are useful as antibacterial agents.

4 Claims, No Drawings

1,2,4-OXADIAZOLONYLACETYL PENICILLINS

This application is a division of Ser. No. 486,542 filed on July 8, 1974 now U.S. Pat. No. 3,929,782 which is a continuation-in-part of Ser. No. 450,929 filed on Mar. 13, 1974, now abandoned.

SUMMARY OF THE INVENTION

This invention relates to new 1,2,4-oxadiazolonylacetyl penicillins and cephalosporins of the formula (I)

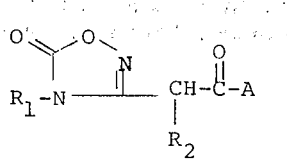

wherein A represents 6-aminopenicillanic acid (6-APA) of the formula (II)

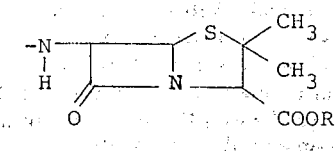

and certain derivatives thereof, or 7-aminocephalosporanic acid (7-ACA) of the formula (III)

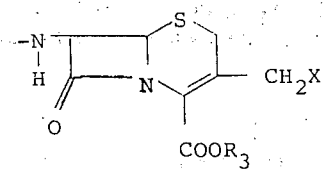

and certain derivatives thereof.

The symbols have the following meaning in formulas I, II and III and throughout this specification.

$R_1$ is hydrogen, lower alkyl, or phenyl-lower alkyl.

$R_2$ is hydrogen, lower alkyl, phenyl, hydroxyphenyl, thienyl, furyl, or pyridyl.

$R_3$ is hydrogen, lower alkyl, phenyl-lower alkyl, benzhydryl, an inorganic or organic salt forming ion, trimethylsilyl, or the group

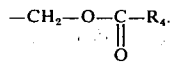

$R_4$ is lower alkyl, phenyl, or phenyl-lower alkyl.

X is hydrogen, lower alkoxy, lower alkanoyloxy, lower alkylmercapto, the radical of a nitrogen base, or heterocyclic thio moieties selected from

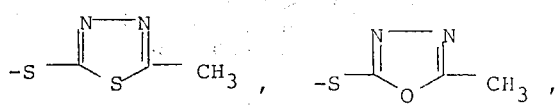

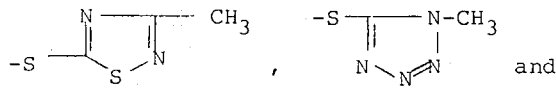

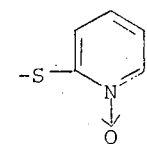

DETAILED DESCRIPTION OF THE INVENTION

The various groups represented by the symbols have the meanings defined below and these definitions are retained throughout this specification.

The lower alkyl groups referred to throughout this specification include straight or branched chain hydrocarbon groups containing 1 to 8 carbon atoms, preferably 1 to 4 carbons. Examples of the type of groups contemplated are methyl, ethyl, propyl, isopropyl, butyl, etc. The lower alkoxy groups include such lower alkyl groups attached to an oxygen, e.g., methoxy, ethoxy, propoxy, etc. The phenyllower alkyl groups include such lower alkyl groups attached to a phenyl, e.g., benzyl, phenethyl, etc.

The salt forming ions represented by $R_3$ may be metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N-lower alkylpiperidines such as N-ethylpiperidine.

The radicals of a nitrogen base represented by X may be radicals of an amine, e.g., methylamine, ethylamine, dimethylamine, triethylamine, dibenzylamine, N,N'-dibenzylpyridinium, pyridinium, 1-quinolinium, 1-picolinium, etc.

The thienyl, furyl and pyridyl groups when employed as the $R_2$ substituents are attached at any available position such as 2- or 3-thienyl, 2- or 3 furyl, 2-, 3-, or 4-pyridyl.

Preferred embodiments of this invention are as follows:

$R_1$ is hydrogen, lower alkyl of 1 to 4 carbons, benzyl or phenethyl.

$R_2$ is hydrogen, lower alkyl of 1 to 4 carbons, phenyl, hydroxyphenyl, thienyl, furyl, or pyridyl.

$R_3$ is hydrogen, lower alkyl of 1 to 4 carbons, benzyl, phenethyl, benzhydryl, aluminum, alkaline earth metal, alkali metal, trimethylsilyl or

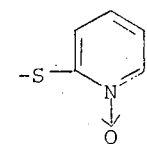

$R_4$ is lower alkyl of 1 to 4 carbons, phenyl, benzyl, or phenethyl.

X is hydrogen, lower alkanoyloxy of 2 to 5 carbons, lower alkoxy of 1 to 4 carbons, lower alkylmercapto of 1 to 4 carbons, pyridinium,

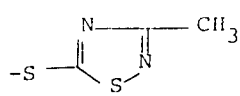 , 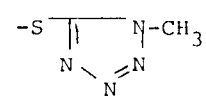 , or 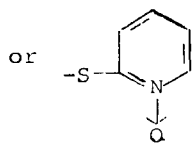 .

The most preferred embodiments are:

$R_1$ is hydrogen or lower alkyl of 1 to 4 carbons, especially hydrogen or methyl.

$R_2$ is phenyl, hydroxyphenyl, thienyl, furyl, or pyridyl, especially phenyl or 2-thienyl.

$R_3$ is hydrogen or benzhydryl, especially hydrogen.

X is hydrogen or lower alkanoyloxy of 2 to 5 carbons, especially

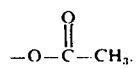

The new compounds of this invention are prepared by the acylation of a 6-aminopenicillanic acid of formula II [which includes 6-aminopenicillanic acid (6APA) and other derivatives] or a 7-aminocephalosporanic acid of formula III [which includes 7-aminocephalosporanic acid (7-ACA), 7-amino-3-desacetoxycephalosporanic acid (7-ADCA) and other derivatives] with a reactive derivative of an acid of the formula (IV) 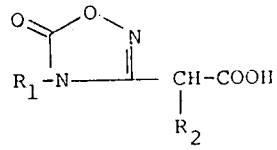

Reactive derivatives of the acid of formula IV include, for example, acid halides, acid anhydrides, mixed anhydrides of the acid of formula IV with carboxylic acid monoesters, trimethylacetic acid or benzoic acid, acid azides, active esters such as cyanomethyl ester, nitrophenyl ester or 2,4-dinitrophenyl ester, or active amides such as acylimidazoles.

The reaction of the compounds of formulas II and III with the acid of formula IV can also be effected in the presence of carbodiimides such as dicyclohexylcarbodiimide, isoxazolium salts such as N-ethyl-5-phenylisoxazolium-3'-sulfonate, or 2-ethoxy-1,2-dihydroquinoline-1-carboxylic acid ester.

The acids of formula IV can be prepared by the following methods.

A substituted acetonitrile of the formula (V)

$NC-CH_2-R_2$ is reacted with hydroxylamine to yield an amidoxime of the formula (VI) 

The amidoxime of formula VI is treated with trichloroacetyl chloride in the presence of a base such as pyridine to yield a substituted-1,2,4-oxadiazole of the formula (VII)

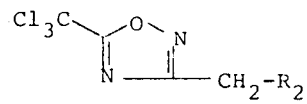

which in turn is treated with NaOH to produce 3-substituted-1,2,4-oxadiazol-5(4H)-one of the formula (VIII)

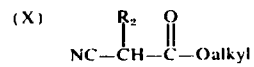

Where $R_1$ is hydrogen, the acid of formula IV is produced by treating the 3-substituted-1,2,4-oxadiazole-5(4H)-one of formula VIII with a solution of butyl lithium and a source of carbon dioxide.

Where $R_1$ is lower alkyl or phenyl-lower alkyl, the acid of formula IV is produced by treating the 3-substituted-1,2,4-oxadiazol-5(4H)-one of formula VIII with a compound of the formula (IX)

$R_1$—halo (halo can be Cl, Br or I)

such as methyl iodide in the presence of a base such as sodium methylate followed by treatment with butyl lithium and carbon dioxide.

Alternatively, the acids of formula IV can be prepared by treating a compound of the formula (X) 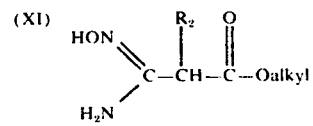

with hydroxylamine to yield a compound of the formula (XI) 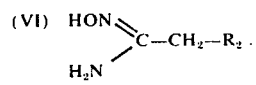

which in turn is treated with trichloroacetyl chloride in the presence of a base such as pyridine to yield a substituted-1,2,4-oxadiazole of the formula (XII)

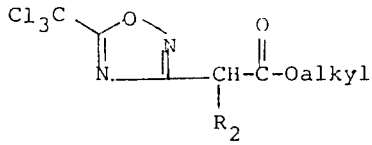

The acids of formula IV where $R_1$ is hydrogen can be prepared by treating the substituted-1,2,4-oxadiazole of formula XII with NaOH. This acid in turn can be reacted with a compound of formula IX in the presence of a base to yield the acid of formula IV where $R_1$ is lower alkyl or phenyl-lower alkyl.

The preferred reactive derivatives of the acids of formula IV are the acid halides, particularly the acid chlorides which can be prepared by reacting the acid with thionyl chloride.

Further process details are also provided in the illustrative examples.

Certain of the compounds of this invention may exist in different optically active forms. The various stereoisomeric forms as well as the racemic mixtures are within the scope of the invention.

The compounds of this invention have a broad spectrum of antibacterial activity against both gram positive and gram negative organisms such as *Staphylococcus aureus*, *Salmonella schottmuelleri*, *Proteus vulgaris*, *Escherichia coli*, *Streptococcus pyogenes*, and especially *Pseudomonas aeruginosa*.

They may be used as antibacterial agents in a prophylactic manner, e.g., in cleaning or disinfecting compositions, or otherwise to combat infections due to organisms such as those named above, and in general may be utilized in a manner similar to cephalothin and other cephalosporins. For example, a compound of formula I or a physiologically acceptable salt thereof may be used in various animal species in an amount of about 1 to 100 mg./kg., daily, orally or parenterally, in single or two to four divided doses to treat infections of bacterial origin, e.g., 2.5 to 5.0 mg./kg. in mice.

Oral forms give prompt high blood levels which are maintained for relatively long periods.

Up to about 600 mg. of a compound of formula I or a physiologically acceptable salt thereof may be incorporated in an oral dosage form such as tablets, capsules or elixirs or in an injectable form in a sterile aqueous vehicle prepared according to conventional pharmaceutical practice.

They may also be used in cleaning or disinfecting compositions, e.g., for cleaning barns or dairy equipment, at a concentration of about 0.01 to 0.5% by weight of such compounds admixed with, suspended or dissolved in conventional inert dry or aqueous carriers for application by washing or spraying. They are also useful as nutritional supplements in animal feeds.

The following examples are illustrative of the invention. All temperatures are on the centigrade scale. Additional variations may be produced in the same manner by appropriate substitution in the starting material.

EXAMPLE 1

6β-[[(4,5-Dihydro-5-oxo-1,2,4-oxadiazol-3-yl) phenylacetyl]-amino]-3,3-dimethyl-7-oxo-4-thia-1-azabicyclo[3.2.0]heptane-2-carboxylic acid a. 3-(Phenylmethyl)-1,2,4-oxadiazol-5(4H)-one 60 g. (0.22 moles) of 3-(phenylmethyl)-5-trichloromethyl-1,2,4-oxadiazole is dissolved in 100 ml. of ethanol. The solution is stirred and 132 ml. (0.264 mole) of 2N sodium hydroxide solution are added dropwise. The temperature of the mixture rises to about 40°. After the addition has been completed, the mixture is stirred for an additional 30 minutes and then concentrated in a rotary evaporator. The residue is treated with water, filtered and the filtrate is acidified with 2N hydrochloric acid. The crystals are filtered under suction, and purified by dissolving in sodium bicarbonate solution, filtering and precipitating with dilute hydrochloric acid. 29.7 g. of 3-(phenylmethyl)-1,2,4-oxadiazol-5-(4H)-one are obtained, m.p. 114°–116°.

b. 4,5-Dihydro-5-oxo-α-phenyl-1,2,4-oxadiazole-3-acetic acid 169.2 g. (0.328 moles + 20 percent) of a 15 percent solution of butyl lithium in hexane is cooled to −60° under a nitrogen atmosphere. At this temperature, a solution of 28.9 g. (0.164 moles) of 3-(phenylmethyl)-1,2,4-oxadiazol-5(4H)-one in 360 ml. of anhydrous tetrahydrofuran is added dropwise with stirring over a period of about 2 hours. A proportionate stream of carbon dioxide is passed through the resulting suspension for a period of 2 hours. The cold bath is removed and the solution is permitted to come to room temperature. The solution is concentrated in a rotary evaporator, the residue is treated with water, the aqueous solution is extracted with ether and the aqueous phase is acidified with 2N hydrochloric acid. This acidified aqueous phase is extracted several times with ether. The combined ether phases are dried with magnesium sulfate and the ether is evaporated. The residue is crystallized by trituration with petroleum ether. 23.9 g. of 4,5-dihydro-5-oxo-α-phenyl-1,2,4-oxadiazole-3-acetic acid are obtained, m.p. 140°–141° (dec.). The product is purified by dissolving in a small amount of water with the addition of sodium bicarbonate and again precipitating with dilute hydrochloric acid. The precipitated product melts at 142°–143° (dec.).

c. 4,5-Dihydro-5-oxo-α-phenyl-1,2,4-oxadiazole-3-acetyl chloride 3.5 g. of the 4,5-dihydro-5-oxo-α-phenyl-1,2,4-oxadiazole-3-acetic acid are stirred with 70 ml. of thionyl chloride and 0.5 ml. of dimethylformamide at a bath temperature of 40°. After 15 minutes, a clear solution results. This is concentrated in a rotary evaporator, the residue is treated with anhydrous chloroform, filtered and again concentrated at room temperature. 4.9 g. of a viscous residue is obtained which still contains some solvent. This crude 4,5-dihydro-5-oxo-α-phenyl-1,2,4-oxadiazole-3-acetyl chloride is used without further purification.

d. 6β-[[(4,5-Dihydro-5-oxo-1,2,4-oxadiazol-3-yl)phenylacetyl]-amino]-3,3-dimethyl-7-oxo-4-thia-1-azabicyclo[3.2.0] heptane-2-carboxylic acid 3.1 g. of 6-aminopenicillanic acid are suspended in 100 ml. of anhydrous chloroform and brought into solution by the addition of 3.05 g. of triethylamine at 0° with stirring. This solution is cooled to −5° and a solution of 4,5-dihydro-5-oxo-α-phenyl-1,2,4-oxadiazole-3-acetyl chloride from part (c) in 50 ml. of anhydrous chloroform is added dropwise. The reaction mixture is stirred for one more hour. 2N hydrochloric acid is added to pH 1.5. After the addition of 30 ml. of ethyl acetate, the phases are separated and the organic phase is extracted twice with dilute sodium bicarbonate solution. The two extracts are combined and extracted once with ether. The aqueous phase is cooled to 0° and acidified with 2N hydrochloric acid to pH 2.5. The precipitate is filtered under suction to 1.2 g. of 6β-[[(4,5-dihydro-5-oxo-1,2,4-oxadiazol-3-yl)-phenylacetyl]amino]-3,3-dimethyl-7-oxo-4-thia-1-azabicyclo[3.2.0]heptane-2-carboxylic acid, m.p.

EXAMPLE 2

3-[(Acetyloxy)methyl]-7β-[[(4,5-dihydro-5-oxo-1,2,4-oxadiazol-3-yl)phenylacetyl]amino]-8-oxo-5-thia-1-azabicyclo[4.2.0]oct-2-ene-2-carboxylic acid By treating 4 g. of the product of Example 1 (c) with 4.5 g. of 7-aminocephalosporanic acid which has been dissolved in 100 ml. of anhydrous chloroform with 6 ml. of triethylamine according to the procedure of Example 1 (d), 2.8 g. of 3-[(acetyloxy)methyl]-7β-[[(4,5-dihydro-5-oxo-1,2,4-oxadiazol-3-yl)phenylacetyl[amino[-8-oxo-5-thia-1-azabicyclo[4.2.0]oct-2-ene-2-carboxylic acid is obtained which decomposes between 95° and 100°.

EXAMPLE 3

3-[(Acetyloxy)methyl]-7β-[[(4,5-dihydro-5-oxo1,2,4-oxadiazol-3-yl)2-thienylacetyl]amino]-8-oxo-5thia-1-azabicyclo[4.2.0]oct-2-ene-2-carboxylic acid a. 5-(Trichloromethyl)-3(2-thienylmethyl)-1,2,4-oxadiazole 290 g. (2.35 moles) of 2-thienylacetonitrile and the equivalent amount of alcoholic hydroxylamine solution are stirred overnight to give 2-thienylacetamidoxime. By concentrating, taking up the residue in anhydrous chloroform, filtering and again concentrating, the crude amidoxime is obtained as a syrup. The syrupy residue is dissolved in 1,000 ml. of anhydrous dioxane and the solution is first treated by the dropwise addition with cooling of 854 g. of trichloroacetyl chloride, then with 380 ml. of pyridine. The mixture is stirred overnight at room temperature. The dioxane is distilled off in a rotary evaporator and 1 liter of water is added to the residue. An oily substance separates which is treated with ether. The ether solution is repeatedly washed with water, then neutralized with saturated sodium bicarbonate solution, again washed with water and dried with magnesium sulfate. After evaporation, the residue is treated with 750 ml. of toluene and refluxed for about 2 hours. Only a small amount of water is removed. The toluene solution is treated with activated carbon, filtered, concentrated and the residue is distilled under vacuum. 258 g. of 5-(trichloromethyl)-3-(2-thienylmethyl)-1,2,4-oxadiazole are obtained, b.p. $_{0.01mm}$ 119°– 122°.

b. 3-(2-Thienylmethyl)-1,2,4-oxadiazol-5(4H)-one 124.8 g. of the 5-(trichloromethyl)-3-(2-thienylmethyl)-1,2,4-oxadiazole obtained in part (a) are converted to 3-(2-thienylmethyl)-1,2,4-oxadiazol-5-(4H)-one by the procedure of Example 1 (a), yield 55.1 g., m.p. 97°–98°.

c. 4,5-Dihydro-5-oxo-α-(2-thienyl)-1,2,4-oxadiazole-3-acetic acid

The 3-(2-thienylmethyl)-1,2,4-oxadiazol-5(4H)-one obtained in part (b) is converted to 4,5-dihydro-5-oxo-α-(2-thienyl)-1,2,4-oxadiazole-3-acetic acid by the procedure of Example 1 (b).

d. 4,5-Dihydro-5-oxo-α-(2-thienyl)-1,2,4-oxadiazole-3-acetyl chloride

The acid obtained in part (c) is converted to the acid chloride with thionyl chloride by the procedure of Example 1 (c).

e. 3-[(Acetyloxy)methyl]-7β-[[(4,5-dihydro-5-oxo-1,2,4-oxadiazol-3-yl)2-thienylacetyl]amino]-8-oxo-5-thia-1-azabicyclo[4.2.0]oct-2-ene-2-carboxylic acid 1.9 g. of the crude 4,5-dihydro-5-oxo-α-(2-thienyl)-1,2,4-oxadiazole-3-acetyl chloride obtained in part (d) is treated with 2 g. of 7-aminocephalosporanic acid in the presence of triethylamine according to the procedure of Example 1 (d) to obtain 1.2 g. of 3-[(acetyloxy)methyl]-7β-[[(4,5-dihydro-5-oxo-1,2,4-oxadiazol-3-yl)2-thienylacetyl]amino]-8-oxo-5-thia-1-azabicyclo[4.2.0]oct-2-ene-2-carboxylic acid.

EXAMPLE 4

3-[(Acetyloxy)methyl]-7β-[[(4,5-dihydro-4-methyl-5-oxo-1,2,4-oxadiazol-3-yl)phenylacetyl]amino]-8-oxo-5-thia-1-azabicyclo[4.2.0]oct-2-ene-2-carboxylic acid a. 4-Methyl-3-(phenylmethyl)-1,2,4-oxadiazol-5(4H)-one 35.2 g. (0.2 moles) of 3-(phenylmethyl)-1,2,4-oxadiazol-5(4H)-one obtained in Example 1 (a) are dissolved in 100 ml of methanol and 110 ml. (0.22 moles) of 2N sodium methylate solution are added. The solution is evaporated to dryness and the residue is dissolved in 200 ml. of anhydrous dimethylformamide. 35.5 g. (0.25 moles) of methyl iodide are added dropwise while cooling with ice water and stirring. The reaction mixture warms slightly and is stirred overnight at room temperature. The reaction mixture is concentrated and the residue is treated with water and acidified with 2N hydrochloric acid. The crystals are filtered under suction, triturated with sodium bicarbonate solution while still moist, again filtered under suction, and washed with water. 33.6 g. of 4-methyl-3-(phenylmethyl)-1,2,4-oxadiazol-5(4H)-one are obtained, m.p. 105°–107°. After recrystallizing twice from isopropanol the m.p. is 110°–112°.

b. 4,.5-Dihydro-4-methyl-5-oxo-α-phenyl-1,2,4-oxadiazole-3-acetic acid

The 4-methyl-3-(phenylmethyl)-1,2,4-oxadiazol-5-(4H)-one obtained in part (a) is converted to the corresponding acid by the procedure of Example 1 (b) using 1.2 moles of butyl lithium per mole of 4-methyl-3-(phenylmethyl)-1,2,4-oxadiazol-5(4H)-one.

c) 4,5-Dihydro-4-methyl-5-oxo-α-phenyl-1,2,4-oxadiazole-3-acetyl chloride

The acid obtained in part (b) is converted with thionyl chloride to the acid chloride by the procedure of Example 1 (c). The crude acid chloride is used further without purification. d) 3-[(Acetyloxy)methyl]-7β-[[(4,5-dihydro-4-methyl-5-oxo-1,2,4-oxadiazol-3-yl)phenylacetyl]amino]-8-oxo-5-thia-1-azabicyclo[4.2.0]oct-2-ene-2-carboxylic acid The acid chloride from part (c) is treated with 7-aminocephalosporanic acid in the presence of triethylamine according to the procedure of Example 1 (d) to obtain 3-[(acetyloxy)-methyl]-7β[[(4,5-dihydro-4-methyl-5-oxo-1,2,4-oxadiazol-3-yl)-phenylacetyl]amino]-8-oxo-5-thia-1-azabicyclo[4.2.0]oct-2-ene-2-carboxylic acid.

EXAMPLE 5

3-[(Acetyloxy)methyl]-7β-[[(4,5-dihydro-5-oxo-1,2,4oxadiazol-3-yl)phenylacetyl]amino]-8-oxo-5-thia-1-azabicyclo[4.2.0]oct-2-ene-2-carboxylic acid a. 3-[(Acetyloxy)methyl]-7β-[[(4,5-dihydro-5-oxo-1,2,4-oxadiazol-3-yl)phenylacetyl]amino]-8-oxo-5-thia-1-azabicyclo[4.2.o]oct-2-ene-2-carboxylic acid, diphenylmethyl ester 4.38 g. (0.01 moles) of 7-aminocephalosporanic acid, diphenylmethyl ester are dissolved in 50 ml. of tetrahydrofuran and 2.64 g. (0.012 moles) of 4,5-dihydro-5-oxo-α-phenyl-1,2,4-oxadiazole-3-acetic acid obtained in Example 1 (b) are added. The solution is cooled to 0°C and a solution of 2.27 g. (0.011 moles) of dicyclohexylcarbodiimide in 40 ml. of tetrahydrofuran is added dropwise over a period of one hour. The mixture is stirred for 90 minutes at 0°, then for 90 minutes at room temperature. The precipitated dicyclohexylurea is removed by filtration under suction and the filtrate is concentrated under vacuum. The residue is dissolved in ethyl acetate, treated with activated carbon, filtered and the filtrate is concentrated to a small volume. Upon the addition of petroleum ether, 6.8 g. of crude 3-[(acetyloxy)-methyl]-7β-[[(4,5-dihydro-5-oxo-1,2,4-oxadiazole-3-yl)-phenylacetyl]amino]-8-oxo-5-thia-1-azabicyclo[4.2.0]oct-2-ene-2-carboxylic acid, diphenylmethyl ester precipitate. The crude product is purified by chromatographing over 500 g. of Kiesel gel (Merck). A mixture of toluene-ethyl acetate (1:3) is used as eluent. 3.6 g. of purified 3-[(acetyloxy)-methyl]-7β-[[(4,5-dihydro-5-oxo-1,2,4-oxadiazol-3-yl)-phenylacetyl]amino]-8-oxo-5-thia-1-azabicyclo[4.2.0]oct-2-ene-2-carboxylic acid, diphenylmethyl ester are obtained.

b. 3-[(Acetyloxy)methyl]-7β-[[(4,5-dihydro-5-oxo-1,2,4-oxadiazol-3-yl)phenylacetyl]amino]-8-oxo-5-thia-1-azabicyclo[4.2.0]oct-2-ene-2-carboxylic acid 3.5 g. of the purified ester from part (a) are added at 0-5° to a mixture of 70 ml. of trifluoroacetic acid and 21 ml. of anisole. The mixture is permitted to stand for 10 minutes at room temperature, concentrated, ether is added to the residue and the resulting precipitate is removed by filtration under suction. The yield is 2.5 g. of 3-[(acetyloxy)methyl]-7β-[[(4,5-dihydro-5-oxo-1,2,4-oxadiazol-3-yl)phenylacetyl]amino]-8-oxo-5-thia-1-azabicyclo-[4.2.0]oct-2-ene-2-carboxylic acid. This crude product is dissolved in ethyl acetate, treated with charcoal and precipitated by the addition of petroleum ether. 2.0 g. of purified 3-[(acetyloxy)methyl]-7β-[[(4,5-dihydro-5-oxo-1,2,4-oxadiazol-3-yl)phenylacetyl]amino]-8-oxo-5-thia-1-azabicyclo[4.2.0]oct-2-ene-2-carboxylic acid are obtained, dec. pt. above 115°.

EXAMPLE 6

3-[[(1-Methyl-1H-tetrazol-5-yl)thio]methyl]-7β-[[(4,5-dihydro-5-oxo-1,2,4-oxadiazol-3-yl)phenylacetyl]amino]-8-oxo-5-thia-1-azabicyclo[4.2.0]oct-2-ene-2-carboxylic acid a. 3-[[(1-Methyl-1H-tetrazol-5-yl)thio]methyl]-7β-[[(4,5-dihydro-5-oxo-1,2,4-oxadiazol-3-yl)phenylacetyl]amino]-8-oxo-5-thia-1-azabicyclo[4.2.0]oct-2-ene-2-carboxylic acid, diphenylmethyl ester 1.32 g. (0.006 moles) of 4,5-dihydro-5-oxo-α-phenyl-1,2,4-oxadiazole-3-acetic acid from Example 1(b) and 2.47 g. (0.005 moles) of 7-amino-3-[[(1-methyl-1H-tetrazol-5-yl)thio]-methyl]-cephalosporanic acid, diphenylmethyl ester are dissolved in 50 ml. of a mixture of equal parts of tetrahydrofuran and methylene chloride and then treated with 1.13 g. (0.0055 moles) of dicyclohexylcarbodiimide at 0° to 5°. The mixture is stirred for 1.5 hours at 0° to 5° and for an additional 1.5 hours at room temperature. The mixture is then filtered and the filtrate is concentrated under vacuum. The residue is dissolved in ethyl acetate, filtered, and concentrated to a small volume. Upon the addition of petroleum ether, a precipitate of 2.3 g. of 3-[[(1-methyl-1-H-tetrazolyl-5-yl)thio]methyl]-7β-[[(4,5-dihydro-5-oxo-1,2,4-oxadiazol-3-yl)phenylacetyl]amino]-8-oxo-5-thia-1-azabicyclo[4.2.0]oct-2-ene-2-carboxylic acid, diphenylmethyl ester; m.p. 114°–120° (dec.); is obtained.

b. 3-[[1-Methyl-1-H-tetrazol-5-yl)thio]methyl]-7β-[[4,5-dihydro-5-oxo-1,2,4-oxadiazol-3-yl) phenylacetyl]amino]-8-oxo-5-thia-1-azabicyclo[4.2.0]oct-2-ene-2carboxylic acid 2.1 g. of the ester from part (a) are added at 0° to 5° to a mixture of 44 ml. of trifluoroacetic acid andd 13.2 ml. of anisole. This mixture is stirred for 10 minutes, concentrated, and the residue is treated with ether. The resulting crude product is treated with 40 ml. of ethyl acetate, filtered, the filtrate is treated with activated carbon and concentrated to about 10 ml. Upon the addition of petroleum ether, a precipitate of 1.3 g. of 3-[[(1-methyl-1H-tetrazolyl-5-yl)thio]methyl]-7β-[[(4,5-dihydro-5-oxo-1,2,4-oxadiazol-3-yl)phenylacetyl]amino]-8-oxo-5-thia-1-azabicyclo[4.2.0]oct-2-ene-2-carboxylic acid; m.p. 130°–133°; is obtained.

EXAMPLES 7–10

Following the procedure of Example 6 but substituting for the 7-amino-3-[[(1-methyl-1-H-tetrazol-5-yl)thio]methyl]-cephalosporanic acid, diphenylmethyl ester the following:

| Ex. | |
|---|---|
| 7 | 7-Amino-3-[[(5-methyl-1,3,4-thiadiazol-2-yl)thio]methyl]-cephalosporanic acid, diphenylmethyl ester |
| 8 | 7-Amino-3-[[(5-methyl-1,3,4-oxadiazol-2-yl)thio]methyl]-cephalosporanic acid, diphenylmethyl ester |
| 9 | 7-Amino-3-[[(3-methyl-1,2,4-thiadiazol-5-yl)thio]methyl]-cephalosporanic acid, diphenylmethyl ester |
| 10 | 7-Amino-3-[[(2-pyridinyl,1-oxide)thio]-methyl]-cephalosporanic acid, diphenylmethyl ester | the following compounds are obtained:

| Ex. | |
|---|---|
| 7 | 3-[[(5-Methyl-1,3,4-thiadiazol-2-yl)thio]-methyl]-7β-[[(4,5-dihydro-5-oxo-1,2,4-oxadiazol-3-yl)phenylacetyl]amino]-8-oxo-5-thia-1-azabicyclo[4.2.0]oct-2-ene-2-carboxylic acid |
| 8 | 3-[[(5-Methyl-1,3,4-oxadiazol-2-yl)thio]-methyl]-7β-[[(4,5-dihydro-5-oxo-1,2,4-oxadiazol-3-yl)phenylacetyl]amino]-8-oxo-5-thia-1-azabicyclo[4.2.0]oct-2-ene-2-carboxylic acid |
| 9 | 3-[[(3-Methyl-1,2,4-thiadiazol-5-yl)thio]-methyl]-7β-[[(4,5-dihydro-5-oxo-1,2,4-oxadiazol-3-yl)phenylacetyl]amino]-8-oxo-5-thia-1-azabicyclo[4.2.0]oct-2-ene-2-carboxylic acid |
| 10 | 3-[[(2-Pyridinyl,1-oxide)thio]methyl]-7β-[[(4,5-dihydro-5-oxo-1,2,4-oxadiazol-3-yl)-phenylacetyl]amino]-8-oxo-5-thia-1-azabicyclo-[4.2.0]oct-2-ene-2-carboxylic acid. |

EXAMPLES 11–15

Following the procedure of Example 4 but substituting the appropriate $R_1$-halo for the methyl iodide in step (a) one obtains the following:

| Ex. | Compound |
|---|---|
| 11 | 3-[(Acetyloxy)methyl]-7β-[[(4,5-dihydro-4-ethyl-5-oxo-1,2,4-oxadiazol-3-yl)phenyl- |

-continued

| Ex. | |
|---|---|
| 12 | acetyl]amino]-8-oxo-5-thia-1-azabicyclo-[4.2.0]oct-2-ene-2-carboxylic acid |
| 12 | 3-[(Acetyloxy)methyl]-7β-[[(4,5-dihydro-4-propyl-5-oxo-1,2,4-oxadiazol-3-yl)phenylacetyl]amino]-8-oxo-5-thia-1-azabicyclo-[4.2.0]oct-2-ene-2-carboxylic acid |
| 13 | 3-[(Acetyloxy)methyl]-7β-[[(4,5-dihydro-4-butyl-5-oxo-1,2,4-oxadiazol-3-yl)phenylacetyl]amino]-8-oxo-5-thia-1-azabicyclo-[4.2.0]oct-2-ene-2-carboxylic acid |
| 14 | 3-[(Acetyloxy)methyl]-7β-[[(4,5-dihydro-4-(phenylmethyl)-5-oxo-1,2,4-oxadiazol-3-yl)phenylacetyl]amino]-8-oxo-5-thia-1-azabicyclo[4.2.0]oct-2-ene-2-carboxylic acid |
| 15 | 3-[(Acetyloxy)methyl]-7β-[[(4,5-dihydro-4-(phenylethyl)-5-oxo-1,2,4-oxadiazol-3-yl)phenylacetyl]amino]-8-oxo-5-thia-1-azabicyclo[4.2.0]oct-2-ene-2-carboxylic acid |

EXAMPLES 16–27

Following the procedure of Example 3 but employing the appropriate substituted-acetonitrile in step (a) in place of the 2-thienylacetonitrile one obtains the following compounds:

| Ex. | Compounds |
|---|---|
| 16 | 3-[(Acetyloxy)methyl]-7β-[[(4,5-dihydro-5-oxo-1,2,4-oxadiazol-3-yl)acetyl]amino]-8-oxo-5-thia-1-azabicyclo[4.2.0]oct-2-ene-2-carboxylic acid |
| 17 | 3-[(Acetyloxy)methyl]-7β-[[(4,5-dihydro-5-oxo-1,2,4-oxadiazol-3-yl)methylacetyl]amino]-8-oxo-5-thia-1-azabicyclo[4.2.0]-oct-2-ene-2-carboxylic acid |
| 18 | 3-[(Acetyloxy)methyl]-7β-[[(4,5-dihydro-5-oxo-1,2,4-oxadiazol-3-yl)ethylacetyl]amino]-8-oxo-5-thia-1-thia-1-azabicyclo[4.2.0]-oct-2-ene-2-carboxylic acid |
| 19 | 3-[(Acetyloxy)methyl]-7β-[[(4,5-dihydro-5-oxo-1,2,4-oxadiazol-3-yl)propylacetyl]amino]-8-oxo-5-thia-1-azabicyclo[4.2.0]-oct-2-ene-2-carboxylic acid |
| 20 | 3-[(Acetyloxy)methyl]-7β-[[(4,5-dihydro-5-oxo-1,2,4-oxadiazol-3-yl)butylacetyl]amino]-8-oxo-5-thia-1-azabicyclo[4.2.0]-oct-2-ene-2-carboxylic acid |
| 21 | 3-[(Acetyloxy)methyl]-7β-[[(4,5-dihydro-5-oxo-1,2,4-oxadiazol-3-yl)butylacetylacetyl]amino]-8-oxo-5-thia-1-azabicyclo-[4.2.0]oct-2-ene-2-carboxylic acid |
| 22 | 3-[(Acetyloxy)methyl-9-7β-[[(4,5-dihydro-5-oxo-1,2,4-oxadiazol-3-yl)3-thienylacetyl]amino]-8-oxo-5-thia-1-azabicyclo[4.2.0]oct-2-ene-2-carboxylic acid |
| 23 | 3-[(Acetyloxy)methyl]-7β-[[(4,5-dihydro-5-oxo-1,2,4-oxadiazol-3-yl)2-furylacetyl]amino]-8-oxo-5-thia-1-azabicyclo[4.2.0]oct-2-ene-2-carboxylic acid |
| 24 | 3-[(Acetyloxy)methyl]-7β-[[(4,5-dihydro-5-oxo-1,2,4-oxadiazol-3-yl)3-furylacetyl]amino]-8-oxo-5-thia-1-azabicyclo[4.2.0]oct-2-ene-2-carboxylic acid |
| 25 | 3-[(Acetyloxy)methyl]-7β-[[(4,5-dihydro-5-oxo-1,2,4-oxadiazol-3-yl)2-pyridylacetyl]amino]-8-oxo-5-thia-1-azabicyclo[4.2.0]oct-2-ene-2-carboxylic acid |
| 26 | 3-[(Acetyloxy)methyl]-7β-[[(4,5-dihydro-5-oxo-1,2,4-oxadiazol-3-yl)3-pyridylacetyl]amino]-8-oxo-5-thia-1-azabicyclo[4.2.0]oct-2-ene-2-carboxylic acid |
| 27 | 3-[(Acetyloxy)methyl]-7β-[[(4,5-dihydro-5-oxo-1,2,4-oxadiazol-3-yl)-4-pyridylacetyl]amino]-8-oxo-5-thia-1-azabicyclo[4.2.0]oct-2-ene-2-carboxylic acid |

Similarly, the penicillanic acid compounds corresponding to the cephalosporanic acid compounds of Examples 11 to 27 are obtained by substituting 6-APA for the 7-ACA.

EXAMPLES 28–47

Following the procedure of Example 1 but employing the 6-aminopenicillanic acid derivatives shown in column 1 for the 6-aminopenicillanic acid one obtains the following compounds shown in column 2:

| Column 1 | Column 2 |
|---|---|
| 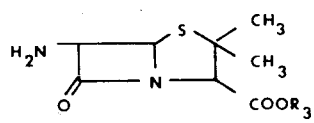 | 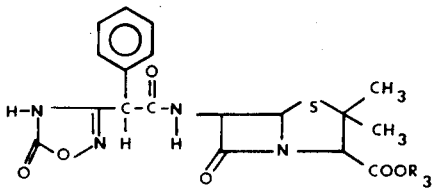 |

| Ex. | $R_a$ |
|---|---|
| 28 | $C_2H_5$ |
| 29 | $i$-$C_3H_7$ |
| 30 | 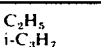 |
| 31 | 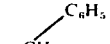 |
| 32 | 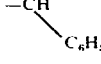 |
| 33 | Al/3 |
| 34 | Na |
| 35 | Ca/2 |
| 36 | Mg/2 |
| 37 | K |
| 38 | $Si(CH_3)_3$ |
| 39 | $[CH_3NH_3]^+$ |
| 40 | $[(C_6H_5CH_2)_2NH_2]^+$ |

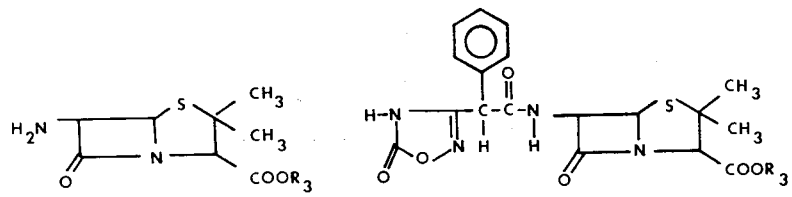

| Ex. | R₃ |
|---|---|
| 41 | $-CH_2-O-\underset{\underset{O}{\|}}{C}-CH_3$ |
| 42 | $-CH_2O-\underset{\underset{O}{\|}}{C}-C_2H_5$ |
| 43 | $-CH_2-O-\underset{\underset{O}{\|}}{C}-C_3H_7$ |
| 44 | $-CH_2-O-\underset{\underset{O}{\|}}{C}-C_4H_9$ |
| 45 | $-CH_2-O-\underset{\underset{O}{\|}}{C}-C_6H_5$ |
| 46 | $-CH_2-O-\underset{\underset{O}{\|}}{C}-CH_2-C_6H_5$ |
| 47 | $-CH_2-O-\underset{\underset{O}{\|}}{C}-(CH_2)_2-C_6H_5$ |

EXAMPLES 48–67

Following the procedure of Example 2 but employing the 7-aminocephalosporanic acid derivatives shown in column 1 for the 7-aminocephalosporanic acid one obtains the following compounds shown in column 2:

| Ex. | R₃ | X |
|---|---|---|
| 48 | H | H |
| 49 | CH₃ | H |
| 50 | C₂H₅ | $-OCH_3$ |
| 51 | i-C₃H₇ | $-OC_2H_5$ |
| 52 | $-CH_2-C_6H_5$ | H |
| 53 | $-CH_2-CH_2-C_6H_5$ | $-O-\underset{\underset{O}{\|}}{C}-CH_3$ |
| 54 | H | $-O-\underset{\underset{O}{\|}}{C}-C_2H_5$ |
| 55 | CH₃ | $-O-\underset{\underset{O}{\|}}{C}-C_3H_7$ |

| | Column 1 | | Column 2 |
|---|---|---|---|

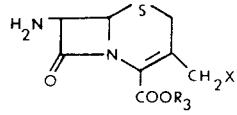

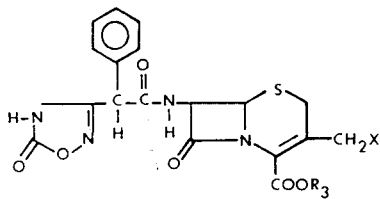

| Ex. | R₃ | | X |
|---|---|---|---|
| 56 | -CH₂-O-C(=O)-CH₃ | | H |
| 57 | Na | | -O-C(=O)-CH₃ |
| 58 | [CH₃NH₃]⁺ | | H |
| 59 | -CH(C₆H₅)(C₆H₅) | | H |
| 60 | | | pyridinium |
| 61 | H | | -S-CH₃ |
| 62 | H | | -S-C₃H₇ |
| 63 | -CH₂-O-C(=O)-C₂H₅ | | -S-(thiadiazole)-CH₃ |
| 64 | -CH₂-O-C(=O)-C₆H₅ | | -S-(oxadiazole)-CH₃ |
| 65 | -CH₂-C₆H₅ | | -S-(thiadiazole)-CH₃ |
| 66 | Si(CH₃)₃ | | -S-(tetrazole)-N-CH₃ |
| 67 | -CH₂-C₆H₅ | | -S-(pyridine N-oxide) |

The 6-aminopenicillanic acid derivatives of column 1 in Examples 28 to 47 and the 7-aminocephalosporanic acid derivatives of column 1 in Examples 48 to 67 can be employed in Examples 11 to 27 to obtain compounds of formula I having the various $R_1$, $R_2$, $R_3$ and X substituents.

What is claimed is:
1. A compound of the formula:

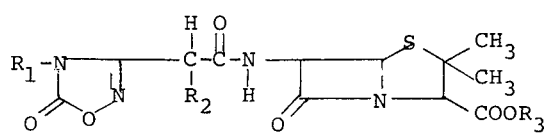

wherein $R_1$ is selected from the group consisting of hydrogen, lower alkyl and phenyl-lower alkyl; $R_2$ is selected from the group consisting of hydrogen, lower alkyl, phenyl, hydroxyphenyl, thienyl, furyl, and pyridyl; and $R_3$ is selected from the group consisting of hydrogen, lower alkyl, phenyl-lower alkyl, benzhydryl, trimethylsilyl, a salt forming ion selected from the group consisting of aluminum, alkali metal, alkaline earth metal, lower alkylamine, phenyl-lower alkylamine and N-lower alkylpiperidine, and -CH₂-

wherein $R_4$ is selected from the group consisting of lower alkyl, phenyl, and phenyl-lower alkyl.

2. The compound of claim 1 wherein $R_1$ is selected from the group consisting of hydrogen, lower alkyl of 1 to 4 carbons, benzyl, and phenethyl; $R_2$ is selected from the group consisting of hydrogen, lower alkyl of 1 to 4 carbons, phenyl, hydroxyphenyl, thienyl, furyl and pyridyl; and $R_3$ is selected from the group consisting of hydrogen, lower alkyl of 1 to 4 carbons, benzyl, phenethyl, benzhydryl, trimethylsilyl, a salt forming ion selected from the group consisting of aluminum, alkali metal, alkaline earth metal, lower alkylamine of 1 to 4 carbons, phenyl-lower alkylamine wherein the alkyl group is of 1 to 4 carbons, and N-lower alkylpiperidine wherein the alkyl group is of 1 to 4 carbons, and

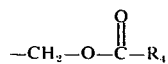

wherein $R_4$ is selected from the group consisting of lower alkyl of 1 to 4 carbons, phenyl, benzyl and phenethyl.

3. A compound as in claim 2 wherein $R_1$ is selected from the group consisting of hydrogen and lower alkyl of 1 to 4 carbons; $R_2$ is selected from the group consisting of phenyl, hydroxyphenyl, thienyl, furyl, and pyridyl; and $R_3$ is selected from the group consisting of hydrogen and benzhydryl.

4. A compound as in claim 3 wherein $R_1$ is hydrogen; $R_2$ is phenyl; and $R_3$ is hydrogen.

* * * * *

UNITED STATES PATENT AND TRADEMARK OFFICE
CERTIFICATE OF CORRECTION

PATENT NO. : 3,959,259
DATED : May 25, 1976
INVENTOR(S) : Hermann Breuer

It is certified that error appears in the above-identified patent and that said Letters Patent are hereby corrected as shown below:

Col. 2, line 25, "phenyllower" should read --phenyl lower --.

Col. 3, line 29, "(6APA)" should read --(6-APA)--.

Col. 7, line 14, "acetyl[amino[" should read --acetyl]amino]--.

Col. 7, line 19, "oxo1,2,4" should read --oxo-1,2,4--.

Col. 7, line 23, "3(2" should read --3-(2--.

Col. 8, line 47, "d)" should start a new line.
Col. 8, line 61, "1,2,4oxadiazol" should read --1,2,4-oxadiazol--.
Col. 10, line 2, "1-H" should read -- 1H --.
Col. 10, line 7, "1-H" should read --1H--.

Col. 10, line 10, "2carboxylic" should read --2-carboxylic--.

Col. 10, line 12, "andd" should read --and--.

Col. 12, second line of example 21, "butylacetyl" should read --hydroxyphenyl--.

Col. 15, example 58, under the heading "$R_3$" "[$CH_3NH_3$]" should read --[$CH_3NH_3$]$^\oplus$--.

Signed and Sealed this

Seventh Day of September 1976

[SEAL]

Attest:

RUTH C. MASON
Attesting Officer

C. MARSHALL DANN
Commissioner of Patents and Trademarks